(12) United States Patent
Stamm (10) Patent No.: US 12,259,383 B2
(45) Date of Patent: Mar. 25, 2025

(54) CHO HOST CELL PROTEIN ASSAY

(71) Applicant: Charles River Laboratories International, Inc., Wilmington, MA (US)

(72) Inventor: Olaf Stamm, Erkrath (DE)

(73) Assignee: Charles River Laboratories International, Inc., Wilmington, MA (US)

( * ) Notice: Subject to any disclaimer, the term of this patent is extended or adjusted under 35 U.S.C. 154(b) by 108 days.

(21) Appl. No.: 17/589,067

(22) Filed: Jan. 31, 2022

(65) Prior Publication Data

US 2022/0155285 A1  May 19, 2022

Related U.S. Application Data

(62) Division of application No. 16/133,828, filed on Sep. 18, 2018, now Pat. No. 11,268,951.

(60) Provisional application No. 62/561,033, filed on Sep. 20, 2017.

(51) Int. Cl.
*G01N 33/541* (2006.01)
*C07K 16/00* (2006.01)
*C07K 16/02* (2006.01)
*C07K 16/18* (2006.01)
*G01N 33/68* (2006.01)

(52) U.S. Cl.
CPC ......... *G01N 33/541* (2013.01); *C07K 16/00* (2013.01); *C07K 16/02* (2013.01); *C07K 16/18* (2013.01); *G01N 33/6803* (2013.01); *C07K 2317/10* (2013.01); *C07K 2317/11* (2013.01); *C07K 2317/20* (2013.01); *C07K 2317/23* (2013.01)

(58) Field of Classification Search
CPC ............ G01N 33/541; G01N 33/542; G01N 33/6803; G01N 33/582; G01N 21/76; C07K 16/00; C07K 16/02; C07K 16/18
See application file for complete search history.

(56) References Cited

U.S. PATENT DOCUMENTS

| 5,080,895 A | 1/1992 | Tokoro |
| 5,736,139 A | 4/1998 | Kink |
| 2014/0017257 A1 | 1/2014 | Jiang |
| 2019/0128903 A1* | 5/2019 | Mao ......................... A61P 3/00 |

OTHER PUBLICATIONS

Karlsson et al. Chicken IgY: utilizing the evolutionary advantage. (World's Poultry Science Journal 60: 341-347 (Sep. 2004).*
Covance Presentation, Anti-HCP Antibody Reagents and Assay Development from a CRO Perspective: Industry Wide Data, Trends, and Recommendations, 27 pages (2017).
Creative Biolabs (Chicken IgY Antibody Production) (undated).

(Continued)

*Primary Examiner* — Gailene Gabel
(74) *Attorney, Agent, or Firm* — MEDLER FERRO WOODHOUSE & MILLS PLLC (57) ABSTRACT

The present invention provides compositions, kits, and methods for the detection of host cell proteins (HCPs) in biological samples. In some embodiments, the present invention utilizes immunization of aves hosts with proteins derived from non-aves host cells to produce aves antibodies specific for non-aves HCPs.

12 Claims, 10 Drawing Sheets

(56) References Cited

OTHER PUBLICATIONS

Han, B. et al. (2017) "Three IgH isotypes, IgM, IgA and IgY are expressed in Gentoo penguin and zebra finch." PLoS One 12:e0173334.
Han, B. et al. (2016) "Multiple IgH isotypes including IgD, subclasses of IgM, and IgY are expressed in the common ancestors of modern birds." J. Immunol. 196:5138-5147.
Rockland Antibodies Assays webpage retrieved from the Internet on Nov. 21, 2018 at https://rockland-inc.com/Product.aspx?id=38578, 2 pages.
Rockland Brochure for Polyclonal Antibodies, 1 page (undated).
Slide for Species Consideration, 1 page (undated).
Stamm and Flad Presentation, "Lightning the black box of HCP Immunoassays—Alternative immunization strategies in combination with innovative characterization tools," 47 pages (2016).
Non-Final Office Action mailed Nov. 24, 2020 in U.S. Appl. No. 16/133,828.
Final Office Action mailed Mar. 11, 2021 in U.S. Appl. No. 16/133,828.
Notice of Allowance and Fee(s) Due mailed Nov. 1, 2021 in U.S. Appl. No. 16/133,828.
Non-Final Office Action mailed Mar. 7, 2024 in U.S. Appl. No. 17/729,528.
Da Silva, et al. IgY: A promising antibody for use in immunodiagnostic and in immunotherapy. Veterinary Immunology and Immunopathology 135: 173-180 (2010).

* cited by examiner

CHO HOST CELL PROTEIN ASSAY

REFERENCE TO RELATED APPLICATIONS

This application is a divisional application of U.S. application Ser. No. 16/133,828, filed Sep. 18, 2018, and claims priority to U.S. Provisional Application No. 62/561,033, filed Sep. 20, 2017, the contents of which are incorporated herein by reference in their entireties.

BACKGROUND OF THE INVENTION

Cell lines are commonly used in the production of recombinant therapeutic proteins and other drugs. In some instances, residual host-cell proteins (HCPs) remain as process impurities in the purified drug product. These residual HCPs can cause adverse reactions in patients receiving the drug. As such, the Food and Drug Administration (FDA) requires that drugs produced in cell lines have a concentration of HCPs that is below a recommended guideline level. This requirement mitigates patient safety concerns by reducing the likelihood of an inflammatory response against the HCPs or other negative side effects.

SUMMARY OF THE INVENTION

The present invention provides compositions, kits, and methods for the detection of host cell proteins (HCPs) in biological samples. In some embodiments, the present invention utilizes immunization of aves hosts with proteins derived from non-aves host cells to produce aves antibodies specific for non-aves HCPs. In some embodiments, the antibodies produced in the aves host recognize the non-aves HCPs with greater specificity and/or greater sensitivity than antibodies produced in a mammalian host against the same set of non-aves HCPs. The present invention therefore provides enhanced methods of detecting HCPs in biological samples, and can thereby enhance the quality control protocols for drugs produced in cell lines.

In some embodiments, the present invention provides methods of detecting an amount of one or more host cell proteins (HCPs) in a sample comprising (a) exposing the sample to a first HCP-specific antibody under conditions sufficient to allow binding of the first HCP-specific antibody to the one or more HCP proteins present in the sample and formation of antibody-HCP protein complexes; (b) processing the sample to remove uncomplexed HCP-specific antibodies and HCP proteins; (c) detecting an amount of the antibody-HCP protein complexes, wherein the first HCP-specific antibodies are produced in an aves host. In some embodiments, the methods further comprise (i) exposing the sample to a second HCP-specific antibody under conditions sufficient to allow binding of the second HCP-specific antibody the one or more HCP proteins in the antibody-HCP protein complexes; and (ii) detecting an amount of the second HCP-specific antibody.

In some embodiments, the second HCP-specific antibody comprises a detectable label. In some embodiments, the detectable label is biotin. In some embodiments, the aves host is a chicken. In some embodiments, the HCPs are derived from a non-aves host. In some embodiments, the non-aves host is a mammalian host selected from the group consisting of hamsters, mice, rats, rabbits, and humans. In some embodiments, the HCPs are derived from a CHO cell. In some embodiments, the HCP-specific antibody is a polyclonal antibody. In some embodiments, the HCP-specific antibody is an IgY isotype.

In some embodiments, the present invention provides kits comprising one or more host cell protein (HCP)-specific antibodies for use in the detection of one or more HCPs in a biological sample, wherein the one or more HCP-specific antibodies are produced in an aves host, and wherein the HCPs are derived from a non-aves host. In some embodiments, the aves host is a chicken and wherein the non-aves host is a mammal. In some embodiments, the HCPs are derived from a CHO cell. In some embodiments, the kit does not comprise one or more HCP-specific antibodies produced in a non-aves host. In some embodiments, the kits comprise one or more HCP-specific antibodies of an IgY isotype. In some embodiments, the kit does not comprise one or more HCP-specific antibodies of a non-IgY isotype.

DETAILED DESCRIPTION OF THE INVENTION

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. All patents and publications cited in this specification are incorporated herein by reference in their entireties.

Unless defined otherwise, all technical and scientific terms used herein have the same meaning as commonly understood by one of ordinary skill in the art to which this disclosure belongs.

As used herein, the singular forms "a," "an" and "the" include plural references unless the content clearly dictates otherwise.

As used herein, the term "and/or" is used in this disclosure to either "and" or "or" unless indicated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As is well known in the art, an "antibody" is an immunoglobulin (Ig) molecule capable of specific binding to a target, such as a carbohydrate, polynucleotide, lipid, or polypeptide, through at least one epitope recognition site, located in the variable region of the Ig molecule. As used herein, the term encompasses not only intact polyclonal or monoclonal antibodies, but also fragments thereof, such as dAb, Fab, Fab', F(ab')$_2$, Fv), single chain (scFv).

The term "antigen" refers to a molecule or a portion of a molecule capable of being bound by an antibody, and additionally capable of being used in an animal to produce antibodies capable of binding to an epitope of that antigen. An antigen may have one or more epitopes.

A "host cell" refers to a cell which has been modified to express or produce one or more heterologous proteins or molecules. The term "host-cell protein" or "HCP" as used herein refers to a protein that is endogenously expressed by a host cell. As such, the term "derived from" when used in a reference to an HCP refers to a protein that is endogenously expressed by the host cell and does not refer to a protein or molecule that is not endogenously expressed by the host cell (e.g., does not refer to a protein or molecule that the host cell has been modified to express).

As used herein, an antibody "specifically binds" or "preferentially binds" if it reacts or associates more frequently, more rapidly, with greater duration, and/or with greater affinity with a particular antigen or antigen epitope than it does with other antigens or antigen epitopes.

A "monoclonal antibody" (mAb) refers to a collection of antibodies that that specifically bind to a single epitope in an antigen. A "polyclonal antibody" refers to a collection of antibodies that bind to a specific antigen, but recognize different epitopes in the antigen.

Antibodies described herein may further comprise a detectable label for use in purification or diagnostic applications. A detectable label may be conjugated to the antibody as a fusion protein or conjugate, e.g., using a linker or linking group. Linking groups include disulfide groups, thioester groups, acid labile groups, photolabile groups, peptidase labile groups, or esterase labile groups, as disclosed in the above-identified patents. Examples of detectable labels suitable for use in the present invention can include, but are not limited to, FLAG tags, poly-histidine tags (e.g. 6×His), cMyc tags, glutathione-S-transferase tags, biotin, fluorescent labels, polymer particles, metal particles, haptens, enzyme labels, luminescent labels, electrochemiluminescent labels, bioluminescent labels, radioisotopes, and oligonucleotides.

Herein, the term "isolated protein" or "isolated polypeptide" refers to a polypeptide or a peptide which either has no naturally-occurring counterpart or has been separated or purified from components which naturally accompany it. In some embodiments, the isolated protein is substantially free from proteins or polypeptides or other contaminants that are found in its natural environment that would interfere with its use (therapeutic, diagnostic, prophylactic, research or otherwise). Typically, the polypeptide or peptide is considered "isolated" when it is at least 70%, by dry weight, free from the proteins and other naturally-occurring organic molecules with which it is naturally associated. Preferably, a preparation of a polypeptide (or peptide) is at least 80%, 85%, more preferably at least 90%, 91%, 92%, 93%, 94%, 95%, 96%, 97%, 98%, and most preferably at least 99%, by dry weight, the polypeptide (peptide).

Methods and Kits for HCP Detection

In some embodiments, the present invention provides methods for detecting one or more HCPs in a sample comprising exposing the sample to an HCP-specific antibody. In particular, the HCP-specific antibodies described herein are produced in an aves host in response to HCPs derived from a non-aves host cell. An aves host refers to any feathered, winged, bipedal, warm-blooded, egg-laying, vertebrate animal and includes any aves species including, but not limited to, ducks, geese, swans, roosters, turkeys, guinea fowl, squabs, pigeons, pheasants, quails, and chickens. In particular embodiments, the HCP-specific antibodies described herein are produced in chickens. A non-aves host may refer to any animal that is not in the aves class. In particular embodiments, a non-aves host refers to a mammalian host or a mammalian host cell. Mammalian hosts include, but are not limited to, mice, rats, hamsters, rabbits, dogs, cats, sheep, pigs, goats, monkeys, and humans. In some embodiments, the HCP-specific antibodies described herein and suitable for use in the methods and kits provided herein are produced in a single type of host species. For example, the HCP-specific antibodies described herein are produced in an aves host and do not comprise HCP-specific antibodies produced in a non-aves hosts. In some embodiments, the HCP-specific antibodies described herein and suitable for use in the methods and kits provided herein comprise antibodies of one isotype. For example, in some embodiments, the HCP-specific antibodies described herein are IgY antibodies and do not comprise other non-IgY isotypes.

In some embodiments, the HCP-specific antibodies of the present invention are produced by immunizing an aves host (e.g., a chicken) with a plurality of HCP antigens. The HCP antigens may be derived from host cells of various species, including mammals, insects, yeasts, and bacteria. In some embodiments, the HCP antigens are derived from Chinese Hamster Ovary (CHO) cells, mouse myeloma cells (e.g., NS0 cells and SP2/0 cells), human embryonic kidney (HEK) cells (e.g., HEK 293 cells), human embryonic retinal (HER) cells, human amniocyte cells (e.g., Glycotope and CEVEC), HeLa cells, Sf9 cells, Sf21 cells, Hi-5 cells, Schneider 2 and 3 cells, or baby hamster kidney (BHK) cells.

In some embodiments, HCP antigens are administered to the aves host without additional processing. In some embodiments, the HCP antigens are fractionated into high and low molecular weight fractions prior to immunization of the aves host. In some embodiments, immunization of the aves host comprises administering the HCP antigens in combination with an adjuvant, such as Complete Freund's Adjuvant (CFA), Incomplete Freund's Adjuvant (IFA), lipopolysaccharide (LPS), or alum. In some embodiments, immunization of an aves host comprises inoculation of the host with the HCP antigens in combination with an adjuvant, followed by one or more additional administrations of the HCP antigens, or "boosts." The one or more boosts of HCP antigen can be administered with or without an adjuvant.

In some embodiments, the HCP-specific antibodies are isolated from the egg yolks of an immunized aves host. In some embodiments, the HCP-specific antibodies are IgY isotype antibodies. Isolation may occur by any means commonly used in the art, including isolation of total antibody protein content from the egg yolks by a series of centrifugation and wash steps. the HCP-specific antibodies may be further purified from the total isolated antibody protein by means commonly used in the art, including ultrafiltration, salt precipitation, alcohol precipitation, gel filtration, anion exchange columns, and/or affinity chromatography using either HCP-antigen specific resins or novel IgY-specific chromatography matrices.

In some embodiments, the HCP-specific antibodies described herein (e.g., HCP-specific antibodies produced in chickens) are capable of detecting HCP antigens with greater sensitivity than previously described methods of HCP detection (e.g., methods using HCP-specific antibodies generated in a mammalian host), providing an advantage over previously existing methods and kits used in the validation and quality control of drug substances produced in cell lines. For example, expression of therapeutic proteins in CHO cells (a cell line derived from hamsters) is a cost effective method for production of commercial quantities of drug substances. However, the manufacturing and purification process of these products leaves the potential for contamination of the purified drug substance with hamster-derived HCPs from the CHO cells. Such contamination can reduce the efficacy of the therapeutic agent and result in adverse toxic or immunological reactions. It is therefore desirable to reduce the HCP contamination of the purified drug substance to the lowest levels that are practical. In order to achieve this reduction, highly sensitive and specific detection of the HCPs is necessary. In some embodiments, the methods and kits provided herein demonstrate an 8- to 9-fold increase in sensitivity compared to currently available methods of HCP detection. In some embodiments, the methods and kits provided herein demonstrate at least a 2-fold, 3-fold, 4-fold, 5-fold, 6-fold, 7-fold, 8-fold, 9-fold, or 10-fold increase in sensitivity compared to currently available methods of HCP detection. Increased sensitivity can be measured by a decrease in the limit of detection achieved with the HCP antibodies. For example, in some embodiments, the methods and kits provided herein have a limit of detection for HCPs of about 8 ng/mL, about 7 ng/mL, about 6 ng/mL, about 5 ng/mL, about 4 ng/mL, about 3 ng/mL, or about 2 ng/mL. In some embodiments, the methods and kits provided herein have a limit of detection for HCPs of less than about 8 ng/mL, less than about 7 ng/mL, less than about 6 ng/mL, less than about 5 ng/mL, less than about 4 ng/mL, less than about 3 ng/mL, or less than about 2 ng/mL. In some embodiments, the methods and kits provided herein have a limit of detection for HCPs between about 2 ng/mL and 6 ng/mL. In some embodiments, the methods and kits provided herein have a limit of detection for HCPs between about 3 ng/mL and 5 ng/mL. In some embodiments, the methods and kits provided herein have a limit of detection for HCPs between about 3.5 ng/mL and 4.5 ng/mL. In some embodiments, the methods and kits provided herein have a limit of detection for HCPs of about 4 ng/mL. In some embodiments, the methods and kits provided herein have a limit of detection for HCPs of about 2 ng/mL.

In some embodiments, the antibodies described herein are capable of reacting with or binding to substantially all of the HCPs that may contaminate the product at the end of the purification processes. In some embodiments, the antibodies described herein are capable of reacting with or binding to at least 90%, at least 91%, at least 92%, at least 93%, at least 94%, at least 95%, at least 96%, at least 97%, at least 98%, or at least 99% of the HCPs that may contaminate the product at the end of the purification processes. In some embodiments, the antibodies described herein are capable of reacting with or binding to a greater fraction of the HCPs that may contaminate the product than other currently available HCP antibodies and detection methods. In some embodiments, the fraction of HCPs that the antibodies described herein are capable of reacting with or binding is at least 10%, at least 20%, at least 30%, at least 40%, at least 50%, at least 60%, at least 70%, at least 80%, at least 90%, or at least 100% greater than the fraction of HCPs bound by previously described HCP antibodies. In some embodiments, the fraction of HCPs that the antibodies described herein are capable of reacting with or binding is at least 2-fold, 3-fold, 4-fold, 5-fold, 6-fold, 7-fold, 8-fold, 9-fold, or 10-fold greater than the fraction of HCPs bound by previously described HCP antibodies.

In some embodiments, the present invention provides methods for detecting one or more HCPs in a sample comprising exposing the sample to an HCP-specific antibody under conditions sufficient to allow binding of the HCP-specific antibody to the one or more HCP proteins present in the sample and for the formation of antibody-HCP protein complexes. The methods described herein comprise immunoassays such as an ELISA or a Western Blot.

In some embodiments, the HCP-specific antibodies may be affixed to a solid support, such as a bead, a plate, or a column. In some embodiments, the HCP-specific antibodies are bound to a plate, and any unbound HCPs or unrelated protein antigens are removed from the assay by one or more wash steps. In such embodiments, the antibody-HCP protein complexes remain affixed to the plate after washing and can be detected by adding a secondary HCP-specific detection antibody comprising a detectable label. Such embodiments employ methods commonly used in sandwich ELISAs.

In some embodiments, a sample comprising one or more HCP antigens is affixed to a solid support (e.g., a plate) and an HCP-specific antibody comprising a detectable label is added to the plate. In such embodiments, unbound HCP-specific antibodies are removed from the plate by one or more wash steps, and the presence of the antibody-HCP protein complexes (e.g., HCP-specific antibodies bound to the HCP antigens affixed to the plate) are detected by virtue of the detectable label present on the antibody. Such embodiments employ methods commonly used in direct ELISAs.

In some embodiments, an unlabeled HCP-specific antibody is incubated in solution with a sample comprising HCP antigens, allowing formation of antibody-HCP antigen complexes in solution. This sample is then added to a plate that has been coated with the HCP antigens. Unbound HCP-specific antibodies present in the solution comprising the antibody-antigen complexes bind to the HCP antigens affixed to the plate, and the antigen-antibody complexes that formed in solution prior to the addition of the sample to the plate are removed by one or more wash steps. The unlabeled HCP-specific antibody bound to the plate-bound antigen is then detected by addition of a secondary antibody specific for the HCP-antibody and comprising a detectable label. In such embodiments, the strength of the signal for detection of the HCP-specific antibody is inversely proportional to the amount of HCP antigen present in the initial sample (e.g., a greater amount of HCP-specific antibody bound to the plate indicates a lesser amount of HCP antigen present in the sample, and vis-versa). Such embodiments employ methods commonly used in competitive ELISAs.

In some embodiments, the present invention provides kits comprising one or more HCP-specific antibodies for use in the detection of one or more HCPs in a sample. In some embodiments, the kits described herein comprise one or more HCP-specific antibodies produced in an aves host. In some embodiments, the kits provided herein comprise one or more HCP-specific antibodies of the IgY isotype. In some embodiments, the kits provided herein do not comprise one or more HCP-specific antibodies produced in a non-aves host. In some embodiments, the kits provided herein do not comprise one or more HCP-specific antibodies of a non-IgY isotype.

The kits described herein may comprise one population of HCP-specific antibodies. Such kits may be suitable for use in a direct ELISA and/or a Western Blot analysis of a sample. In such embodiments, the population of HCP-specific antibodies may further comprise a detectable label. In some embodiments, the kits described herein may comprise two populations of HCP-specific antibodies. Such kits may be suitable for use in a direct ELISA, a sandwich ELISA, a competitive ELISA, or a Western blot analysis of a sample. In such embodiments, one of the two populations of HCP-specific antibodies may further comprise a detectable label. In such embodiments, each of the two populations of HCP-specific antibodies may further comprise a detectable label.

In some embodiments, the kits provided herein further comprise one or more buffers suitable for use in the methods described herein. For example, kits may further comprise a buffer for re-suspending or diluting the HCP antibodies. In some embodiments, kits may further comprise one or more wash buffers. Suitable buffers are known in the art and include, but are not limited to, buffered saline solutions (e.g., HBSS, PBS, TBS, bi-carbonate buffered saline, etc.), cell culture media, saline solutions, and the like.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1

Production of HCP-Specific Antibodies in Chickens
Chicken Immunization 30-40 week old hens were divided into group of 4 hens/group. Initial test bleeds were taken from the wing vein of each hen and tested in the HCP ELISA described in Example 2. If birds showed a positive result on the HCP ELISA, they were removed from the project.

Figure 1:
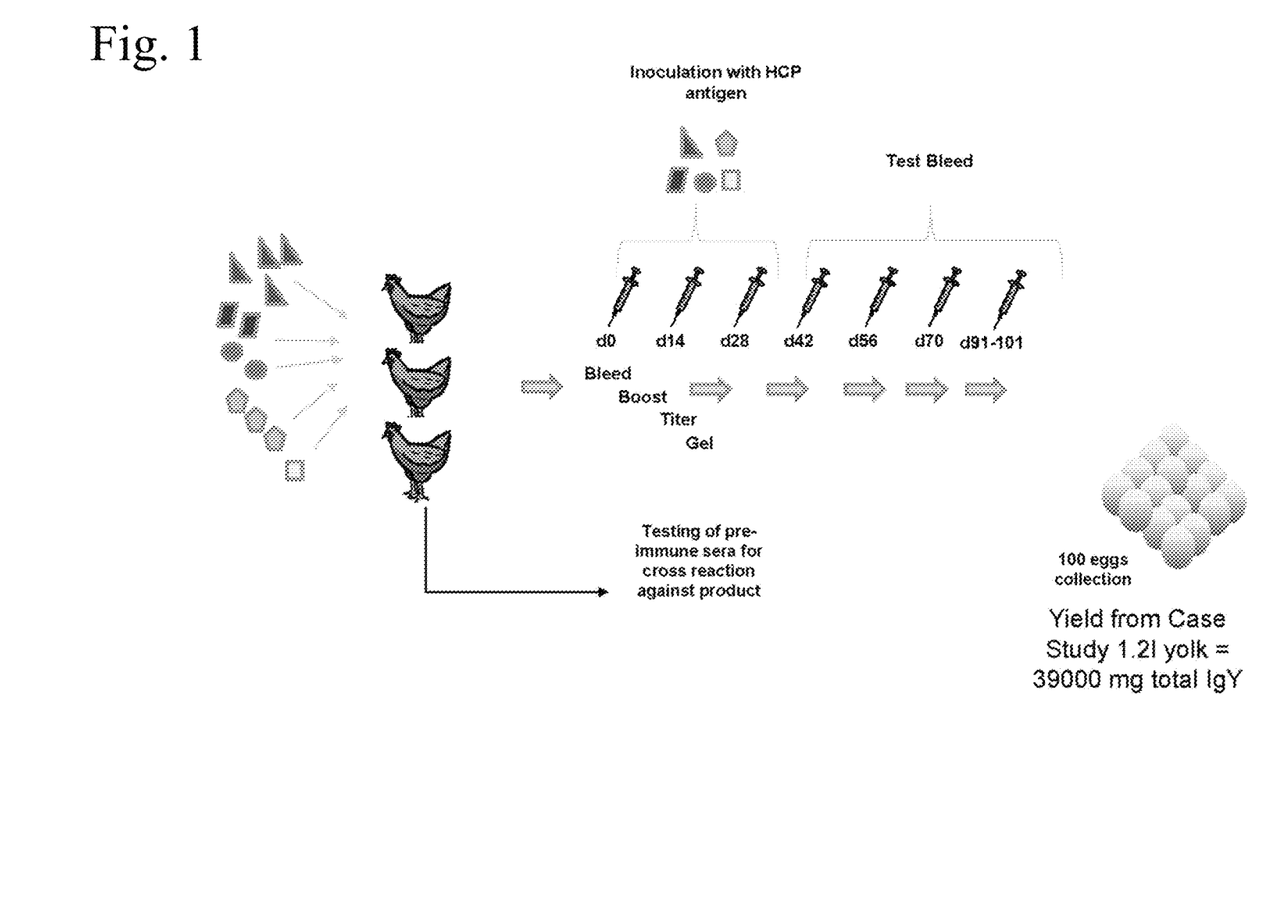
FIG. 1 illustrates an exemplary protocol for immunization of chickens with host cell proteins (HCPs) derived from mammalian cells.

After initial testing, birds were inoculated intramuscularly with 0.5 mL of HCP and Freund's CFA. After two weeks, test bleeds were taken from each hen. Each hen was then boosted with 0.5 mL of CFA in Incomplete Adjuvant. After two weeks, a second test bleed was taken from each hen. Each hen was boosted for a second time with 0.5 mL of CFA in Incomplete Adjuvant. Two weeks after the second boost, eggs were collected on a weekly basis until 100 eggs were collected. A schematic of the immunization protocol is shown in FIG. 1.

IgY Antibody Isolation and Purification

IgY antibodies are isolated from egg yolks obtained from HCP-immunized hens. Briefly, egg yolks were separated from the albumen using an autoclaved egg separator. Yolks from each treatment group were combined, mixed, and diluted 1:10 in deionized water. The pH of the egg yolk solution was lowered to 5.0 (±0.2) by adding 5 M HCl. Diluted egg yolkds were incubated overnight at 4° C.

Figure 2:
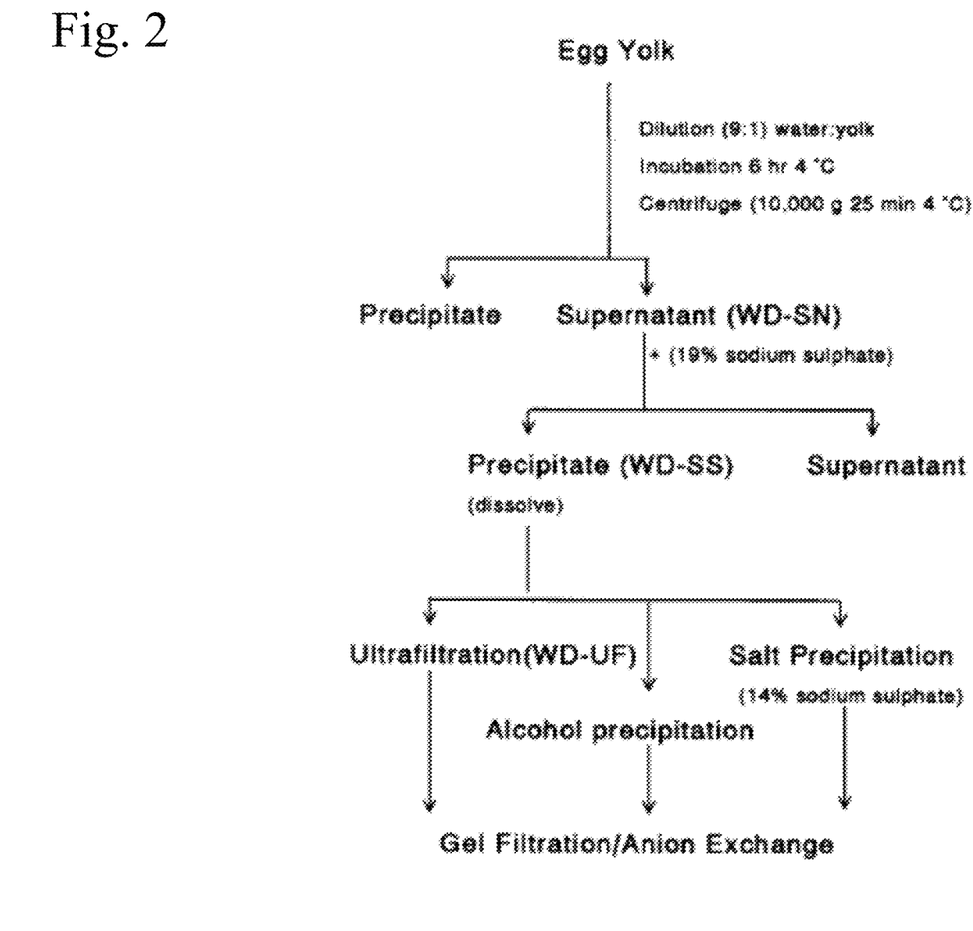
FIG. 2 illustrates the work-flow for isolation of IgY antibodies from chicken egg yolks.
Figure 3:
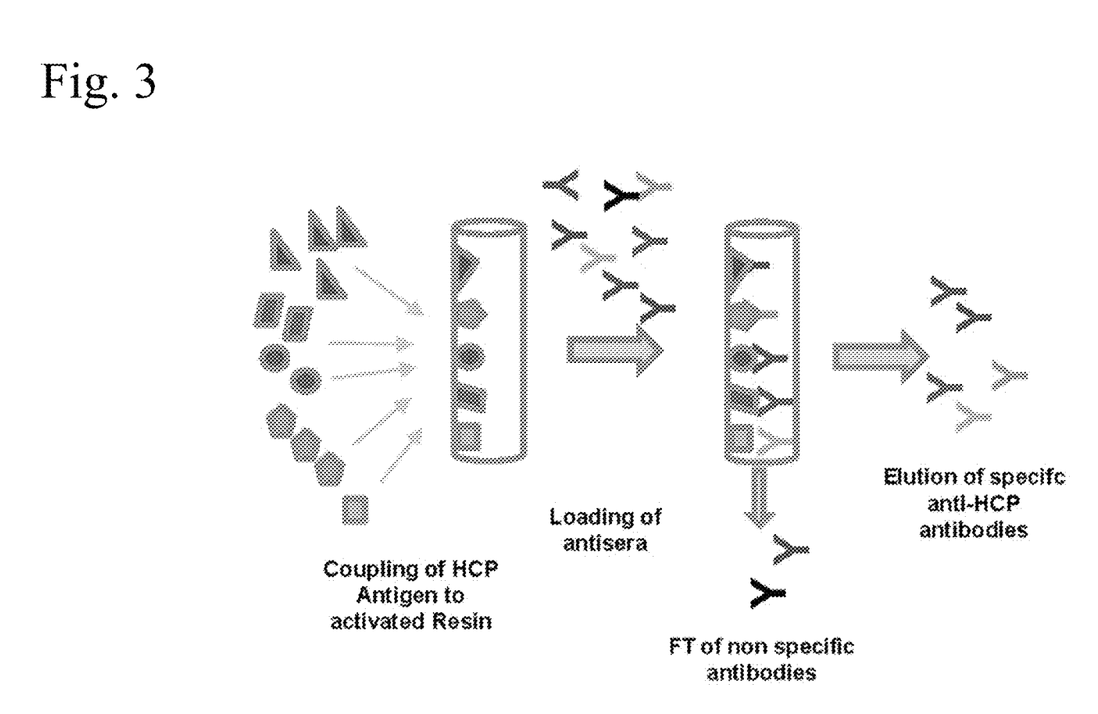
FIG. 3 illustrates an exemplary schematic for purification of HCP-specific antibodies isolated from chicken egg yolks.

The next day, the liquid portion of each yolk mixture was collected and centrifuged at 10,000 rpm for 10 minutes at 4° C. The top liquid layer was removed and centrifuged again at 10,000 rpm for 10 minutes at 4° C. Solid portions were discarded. After the second spin, supernatants were collected and strained through gauze. The pH of the pooled supernatants was adjusted to 7.0 (±0.2) using 1 M NaOH. Neutralized supernatants were concentrated by Biomax cassette or dialysis tubing and immediately filtered through a 0.45 μm filter. Protein content was assayed and antibody isolates were frozen at −20° C. A schematic of the isolation protocol is shown in FIG. 2. HCP-specific antibodies may be further purified by gel filtration, anion exchange, and/or affinity chromatography using IgY-specific resins. A schematic of the purification protocol is shown in FIG. 2 and FIG. 3

Example 2

Characterization and Validation of HCP-Specific IgY Antibodies

Experiments were performed to characterize and validate the IgY antibodies produced according to Example 1. Proteins of the HCP sample (Antigen 07 HCP N02) were separated by high resolution analytical 2D-PAGE (20×20 cm). Proteins were visualized by silver staining (gel), colloidal gold staining (Blot), and immunodetection (Western Blot). Resulting images were evaluated side-by-side, where possible as overlaid images and according to the detected spot number.

In total, one silver stained gel, one colloidal gold stained blot and two Western Blots, using either a commercially available antiserum (Cygnus, P10988) or a chicken antibody (anti 07 HCP N02), were generated. The silver stained gel served as a control for the total number of present spots and the colloidal gold stained blot served as a control for the blotting efficiency indicating the availability of the total spot number after blotting. Spots were counted for all detection modes and the ratios were generated. Results from spot count are summarized in Table 1.

TABLE 1

Spot Count and Ratio Summary

| Antigen 07 HCP N02 | Number of Detected Spots | | | Ratio spot count |
| --- | --- | --- | --- | --- |
| | Silver Stain | Colloidal gold stain | WB | WB to silver staining [5] |
| Antiserum Chicken anti 07 HCP N02 | 1821 | 1762 | 1597 | 88 |
| Antiserum P10988 | | | 191 | 10 |

Figure 4:
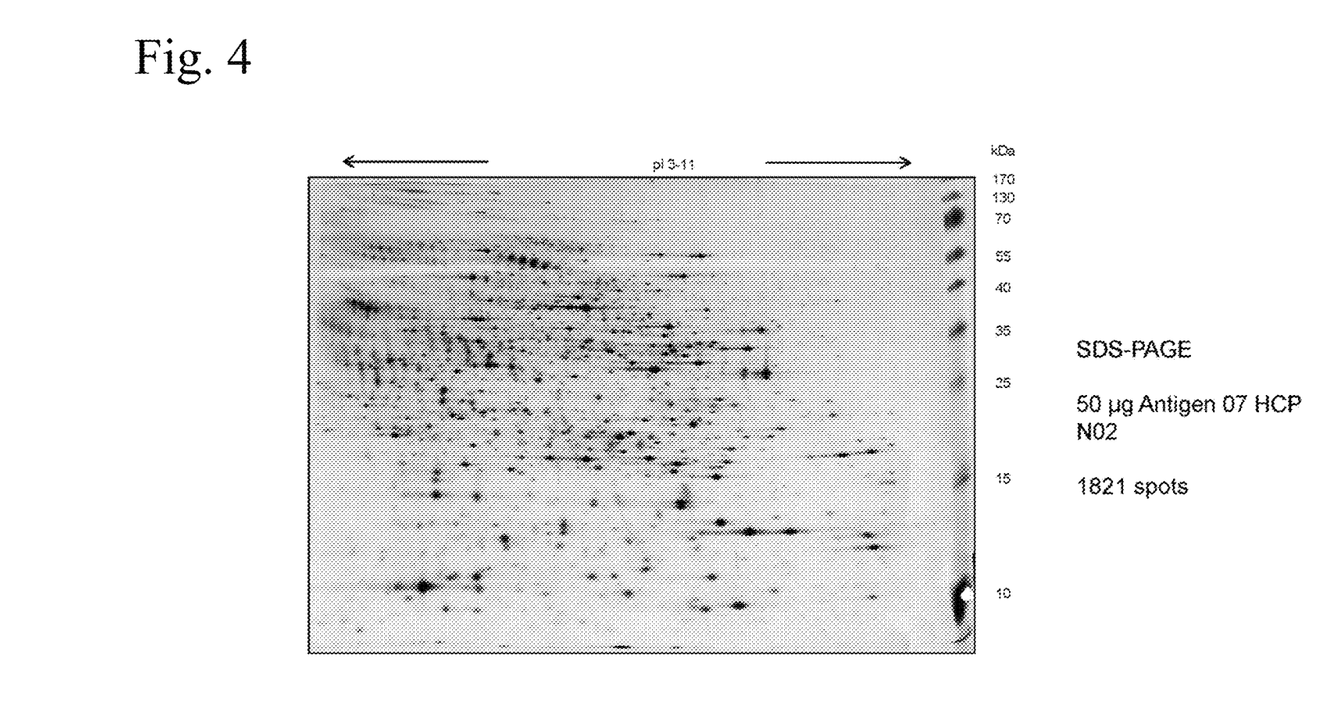
FIG. 4 illustrates quantification of total protein spots in a sample by silver-stained gel.
Figure 5:
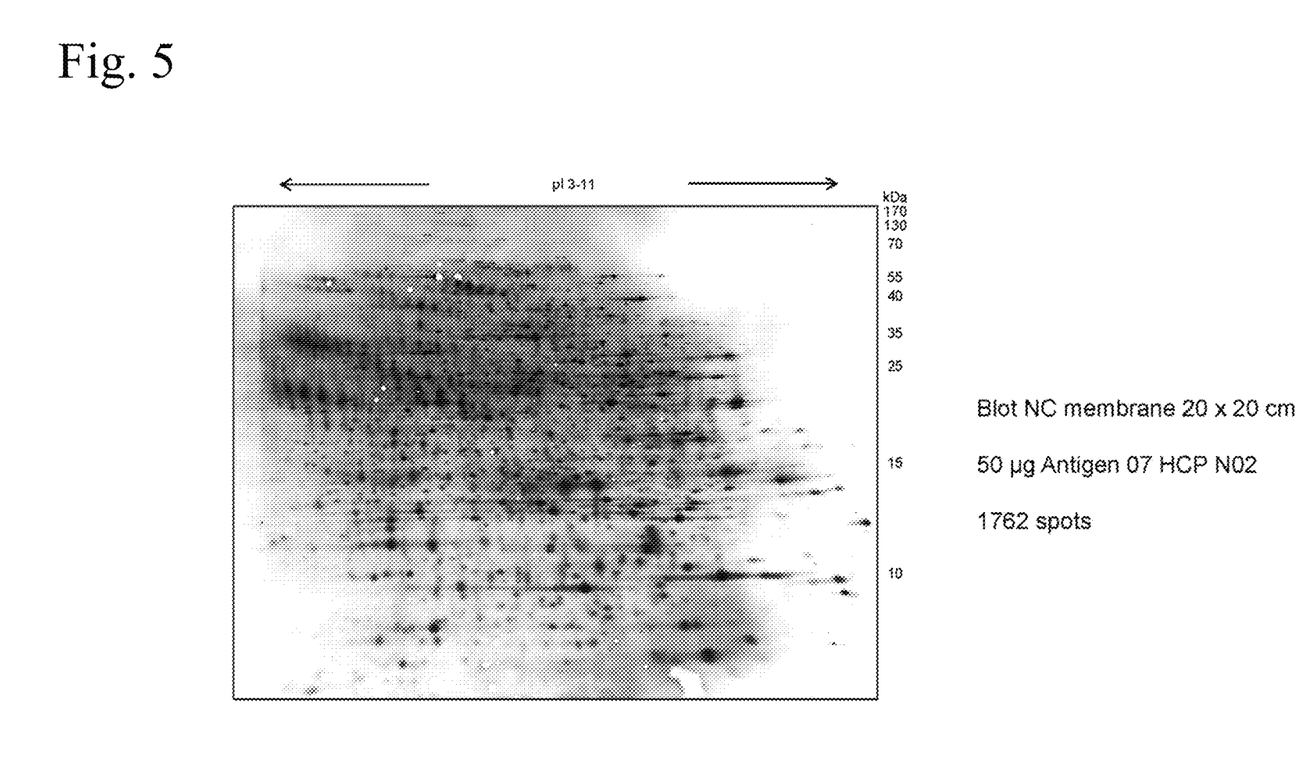
FIG. 5 shows a colloidal gold-stained gel and serves as a control for blotting efficiency.

Excellent quality images were obtained for the silver stained gel (FIG. 4) and the colloidal gold stained blot (FIG. 5) as indicated by the highly resolved spot patterns and the determined total spot number of 1821 and 1762, respectively. The number of spots determined for the colloidal gold stained blot indicated an excellent blotting efficiency. This was a prerequisite to enable the antibody/antiserum the detection of most of the proteins present in the HCP sample.

Figure 6:
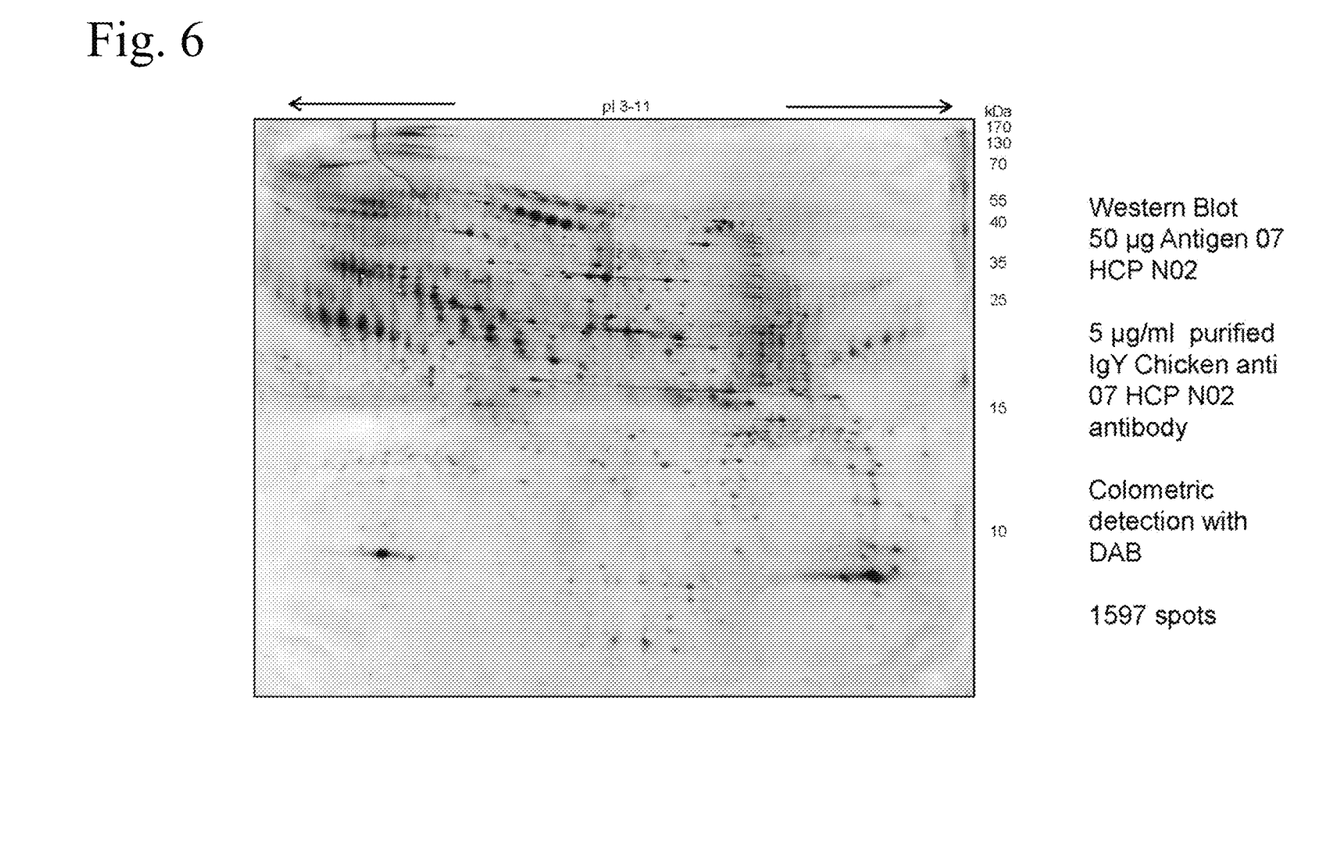
FIG. 6 shows the total protein spots observed in a sample blotted with an anti-HCP antibody produced in chickens.
Figure 7:
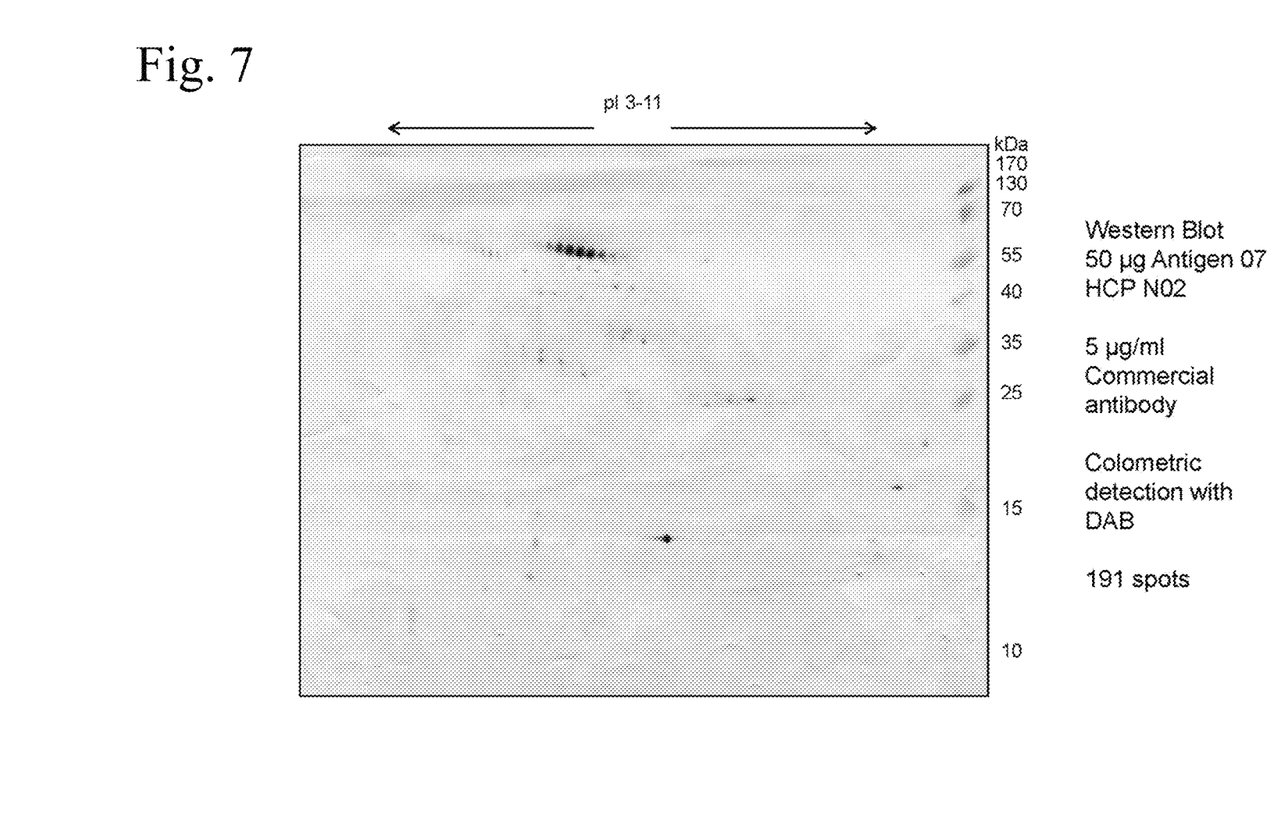
FIG. 7 shows the total protein spots observed in a sample blotted with a commercially available anti-HCP antibody produced in goats.
Figure 8:
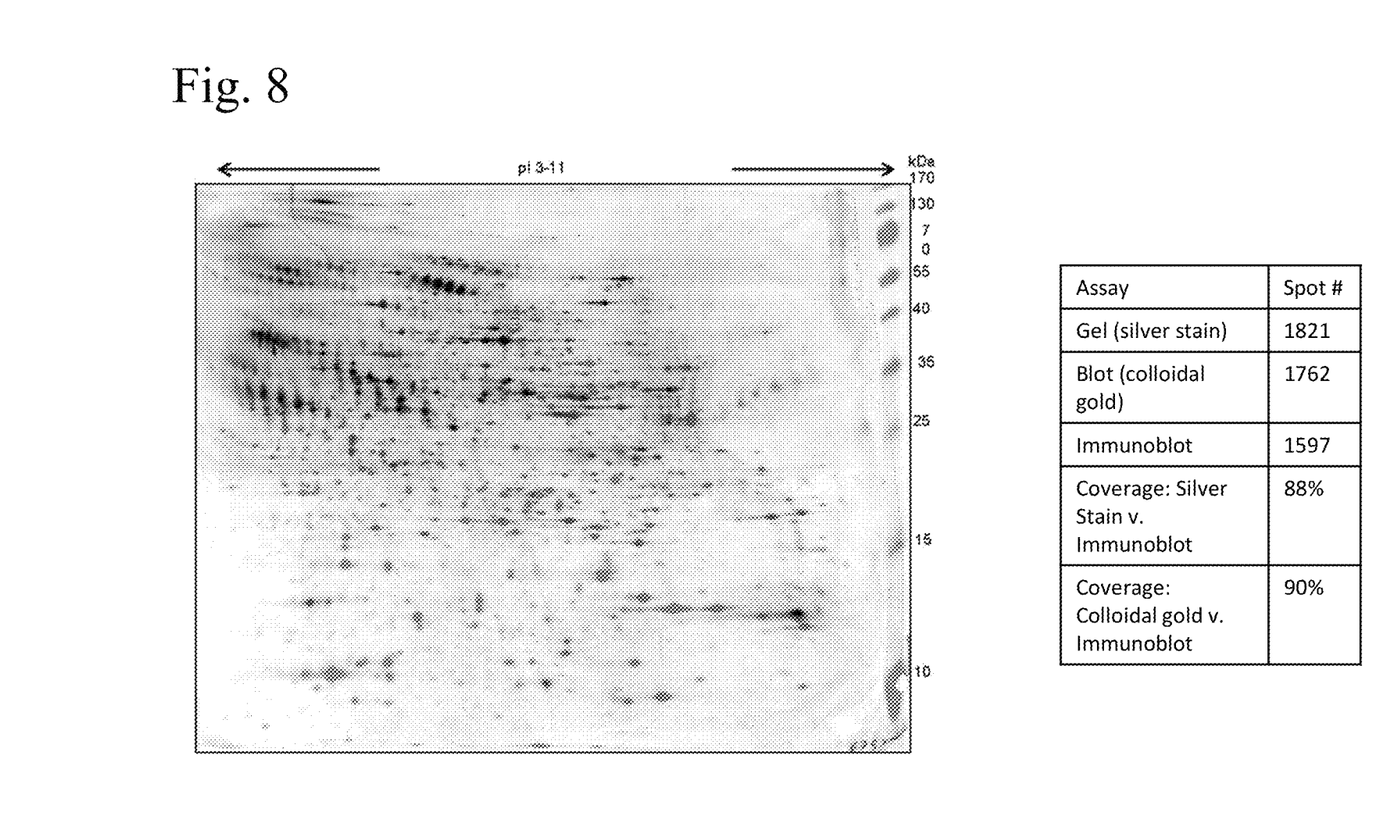
FIG. 8 shows an overlay of silver-stained gels and immunoblots with chicken anti-HCP antibodies.
Figure 9:
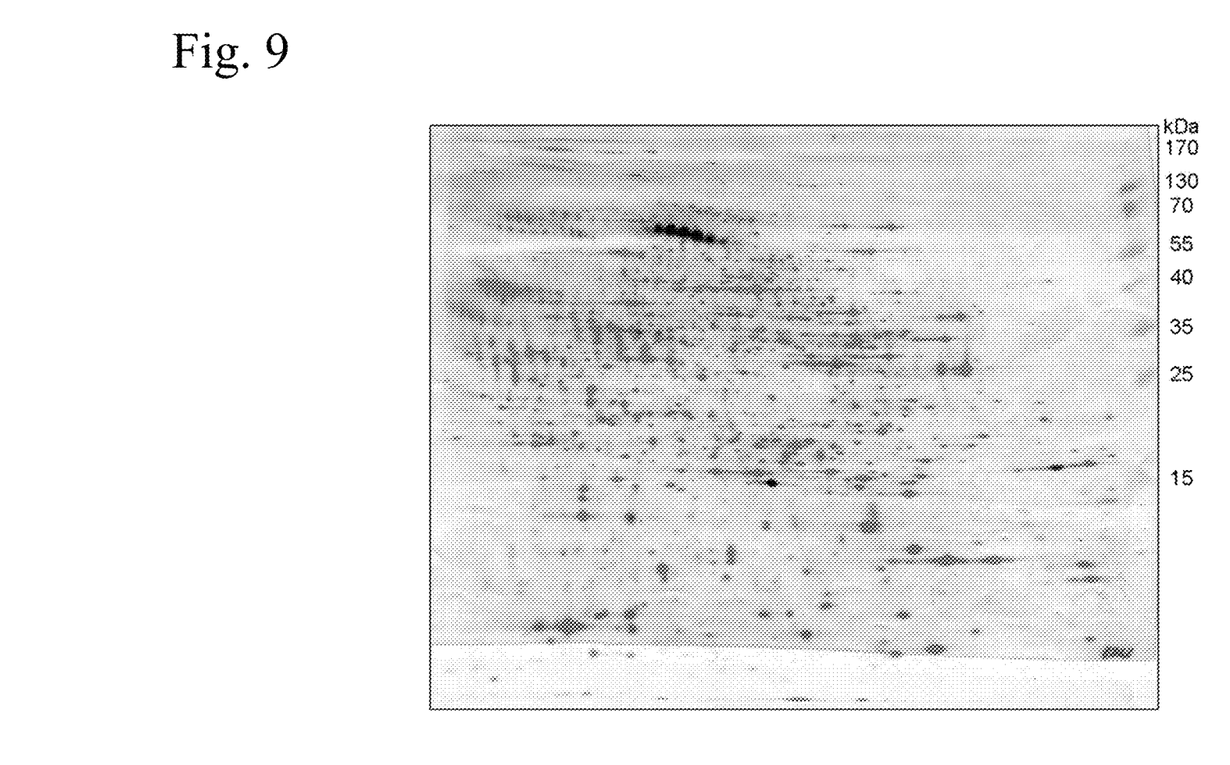
FIG. 9 shows an overlay of silver-stained gels and immunoblots with goat anti-HCP antibodies

Immunoblotting using the commercially available Cygnus antiserum yielded a spot count of 191 spots and a corresponding spot count ratio towards the silver stained gel of around 10% (FIG. 7). Overlays of silver-stained gels and immunoblots with commercial antiserum are shown in FIG. 9. Using the provided chicken antibody yielded a spot count of 1597 spots and a corresponding spot count ratio of around 88% (FIG. 6). Overlays of silver-stained gels and immunoblots with chicken anti 07 HCP N02 antiserum are shown in FIG. 8.

Experiments were performed to characterize and validate the IgY antibodies produced according to Example 1. Briefly, microtiter plates (MTPs) were coated with 100 μL of an anti-HCP-IgY antibody solution (H07 HCP N02 IgY, 2 μg/mL in PBS, pH 7.4). Coated MTPs were incubated at 5° C.±3° C. After washing, plates were blocked with 300 μL of PBS+0.1% Tween 20 and incubated at room temperature for 60 minutes. After incubation, plates were washed and 100 μL of the following test samples and controls listed below were added to the plate.
- (a) Standards: purified CHO HCP (H07 HCP N02), diluted from 5000 ng/mL to 1 ng/mL in PBS+0.1% Tween 20;
- (b) Dilution Buffer (1 ng/mL in PBS+0.1% Tween 20) with and without CHO HCP spike;
- (c) Blank controls;
- (d) Test sample (Rituximab (MabThera), diluted to 1 mg/mL in PBS+0.1% Tween 20 with and without CHO HCP spike. CHO HCP was spiked in at 5, 7, 10, 25, 50, and 100 ng/mL.

Figure 10:
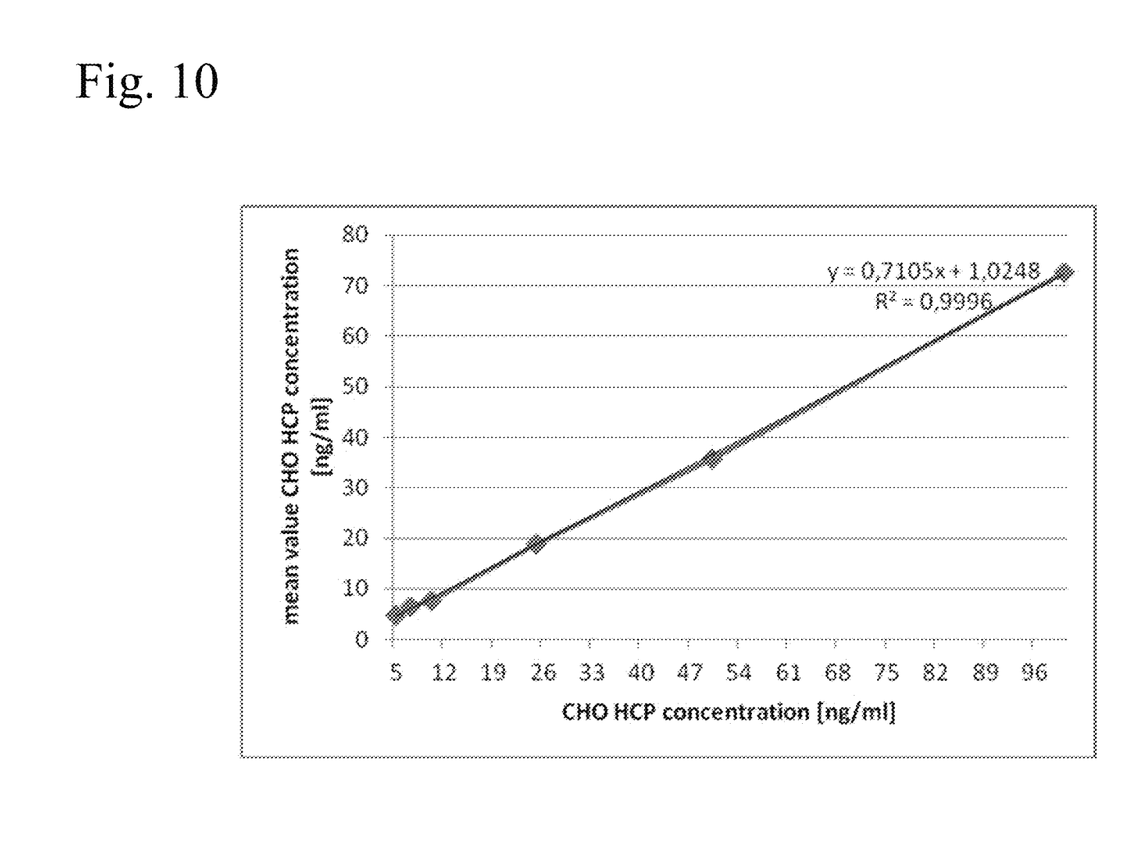
FIG. 10 shows results of the linearity validation of an HCP-IgY ELISA.

Plates were incubated at room temperature for 60 minutes and washed again. 100 μL of biotin-conjugated detection antibody (H07 HCP N02 IgY-biotinylated, 0.5 μg/mL in PBS+0.1% Tween 20) was added to each well. After incubating for 60 minutes at room temperature, plates were washed to remove unbound detection antibody. 100 μL of HRP-conjugated streptavidin (diluted 1:2000 in PBS+0.1% Tween 20 from a working dilution of 0.5 U/mL) was added to each well. Plates were again incubated at room temperature for 60 minutes and washed. 100 μL of TMB substrate was added to each well, and plates were incubated for 30 minutes. After 30 minutes, 100 μL of stop solution was added to each well and absorbance was read at 450 nm/630 nm. The results of the HCP-IgY ELISA validation are shown in FIG. 10. The correlation coefficient calculated for the correlation between the measured CHO HCP concentrations and the spike concentrations was 0.999, demonstrating a strong correlation between the two. Further, the measured concentrations of HCP in the control buffer wells was below the quantitation limit of 5 ng/mL, demonstrating the specificity of the HCP-IgY ELISA. Additional parameters measured in the validation assays are shown in Tables 2A and 2B.

TABLE 2A

IgY Antibody Validation Parameters

| Validation Parameter | Validation acceptance criteria | Results |
|---|---|---|
| Linearity | Coefficient of correlation (r) must be ≥ 0.990 | The coefficient of correlation (r) was 1.00 using HCP - concentrations from 4 ng/mL to 250 ng/mL |
| Quantitation limit and range | The lower/higher limit of quantitation is the lowest/highest amount of analyte in a sample which can be quantitatively determined with suitable precision and accuracy (recovery). The quantitation limits are defined as the lower and highest values of the linearity for which the accuracy has to be ≥ 75% and ≤ 125% and the CV has to be ≤ 25% | Lower quantitation limit: 4 ng/mL (CV = 6%) Upper quantitation limit: 250 ng/mL (CV = 4%) Range: 4 ng/mL-250 ng/mL |
| Specificity | The signal of the test item matrix without spike must be below the quantitation limit | The HCP concentration of the test item matrix without spike was below the quantitation limit of 4 ng/mL. Therefore the specific binding of HCP was shown |

TABLE 2B

IgY Validation parameters

| Validation Parameter | Validation acceptance criteria | Results |
|---|---|---|
| Accuracy | The mean values of a 3-fold determination of the spiked test items are not allowed to deviate more than 25% from the value of the spike buffer, meaning the accuracy has to be ≥ 75% and ≤ 125% | 4 ng/mL (n = 3): (99%-112%) 25 ng/mL (n = 3): (98%-104%) 250 ng/mL (n = 3): (84%-90%) |
| Precision/ Repeatability | CV ≤ 25% | CV (n = 6): 5% |
| Intermediate Precision | CV ≤ 25% | CV (n = 6): 6% |
| Robustness | Robust regarding the incubation time of standards, controls, and samples on the ELISA plates and incubation conditions of the substrate. All system suitability criteria must be fulfilled. | Ongoing |

The invention claimed is:

1. A kit comprising one or more host cell protein (HCP)-specific antibodies for use in the detection of one or more HCPs in a biological sample,
   wherein the HCPs are derived from a non-aves host,
   wherein the one or more HCP-specific antibodies are produced in an aves host and are an IgY isotype,
   wherein the one or more HCP-specific antibodies are capable of detecting at least 85% of the HCP proteins present in the sample,
   wherein the one or more HCP-specific antibodies comprise a detectable label, and
   wherein the detectable label is biotin, an enzyme label or a fluorescent label.

2. The kit of claim 1, wherein the HCPs are derived from a CHO cell.

3. The kit of claim 1, wherein the aves host is a chicken.

4. The kit of claim 1, wherein the kit does not comprise one or more HCP-specific antibodies produced in a non-aves host.

5. The kit of claim 1, wherein the kit does not comprise one or more HCP-specific antibodies of a non-IgY isotype.

6. The kit of claim 1, wherein one or more HCP-specific antibodies is a polyclonal antibody.

7. A kit comprising a first and a second host cell protein (HCP)-specific antibody for use in the detection of one or more HCPs in a biological sample,
    wherein the HCPs are derived from a non-aves host,
    wherein the first and the second HCP-specific antibodies are produced in an aves host and are an IgY isotype, and
    wherein the first HCP-specific antibody is capable of detecting at least 85% of the HCP proteins present in the sample,
    wherein the second HCP-specific antibody comprises a detectable label, and
    wherein the detectable label is biotin, an enzyme label, or a fluorescent label.

8. The kit of claim 7, wherein the HCPs are derived from a CHO cell.

9. The kit of claim 7, wherein the aves host is a chicken.

10. The kit of claim 7, wherein the kit does not comprise one or more HCP-specific antibodies produced in a non-aves host.

11. The kit of claim 7, wherein the kit does not comprise one or more HCP-specific antibodies of a non-IgY isotype.

12. The kit of claim 7, wherein first and second HCP-specific antibodies are polyclonal antibodies.

\* \* \* \* \*